United States Patent
Kumar et al.

(10) Patent No.: US 10,221,165 B2
(45) Date of Patent: Mar. 5, 2019

(54) FLAVONE BASED EGFR INHIBITORS AND PROCESS FOR PREPARATION THEREOF

(71) Applicant: Council of Scientific and Industrial Research, New Delhi (IN)

(72) Inventors: Pradeep Kumar, Pune (IN); Jignesh Kantilal Parikh, Pune (IN); Eeshwaraiah Begari, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/548,536

(22) PCT Filed: Feb. 3, 2016

(86) PCT No.: PCT/IN2016/050037
§ 371 (c)(1),
(2) Date: Aug. 3, 2017

(87) PCT Pub. No.: WO2016/125186
PCT Pub. Date: Aug. 11, 2016

(65) Prior Publication Data
US 2018/0016268 A1    Jan. 18, 2018

(30) Foreign Application Priority Data
Feb. 3, 2015   (IN) .............................. 305/DEL/2015

(51) Int. Cl.
C07D 417/04       (2006.01)
A61K 31/427       (2006.01)

(52) U.S. Cl.
CPC ................... *C07D 417/04* (2013.01)

(58) Field of Classification Search
CPC ... C07D 417/04; C07D 277/42; A61K 31/427
USPC .......................................... 548/191; 514/370
See application file for complete search history.

(56) References Cited

U.S. PATENT DOCUMENTS 9,090,583 B2 *   7/2015   Ding .................... C07D 311/30
2014/0038940 A1   2/2014   Xu et al.

FOREIGN PATENT DOCUMENTS

WO        2013184766       12/2013

\* cited by examiner

Primary Examiner — Charanjit Aulakh
(74) Attorney, Agent, or Firm — Carmody Torrance Sandak & Hennessey LLP

(57) ABSTRACT

The present invention discloses a novel EGFR inhibitor compound of formula (1), process for preparation thereof and methods of treating abnormal cell growth in mammals by administering the compounds of formula ($^1$) wherein, R is selected from hydrogen, alkyl, nitro, halogens such as chlorine, bromine, fluorine and iodine; $R_1$=hydrogen, alkyl, alkoxy, aryl, nitro, halogens such as chlorine, bromine, fluorine and iodine, trifluoromethyl, thioalkyl, trifluromethoxy, trialkylsilyl.

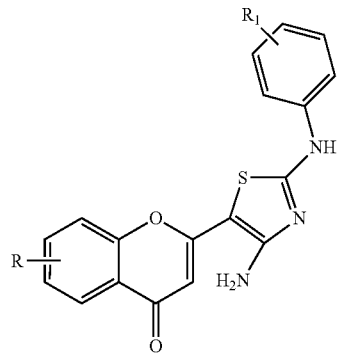

Formula (I)

9 Claims, 1 Drawing Sheet

FLAVONE BASED EGFR INHIBITORS AND PROCESS FOR PREPARATION THEREOF

FIELD OF THE INVENTION

The present invention relates to a novel flavone based EGFR inhibitor compound of formula (I), process for preparation thereof and method for treating abnormal cell growth in mammals by administering said compound of formula (I). The present invention further relates to a pharmaceutical composition of compound of formula (I) for treating abnormal cell growth in mammals.

BACKGROUND OF THE INVENTION

The identification of (epidermal growth factor) EGFR as an oncogene led to the development of anticancer therapeutics called "EGFR inhibitors" that includes gefitinib, erlotinib, afatinib, and icotinib for lung cancer, and cetuximab for colon cancer. EGFR is a transmembrane tyrosine kinase receptor that plays a central role in regulating cell division and death.

There is literature evidence available that flavones are potential anti cancer agents. Flavone moiety is cancer preventing agent, which is available as natural product, so is expected to posses less side effects. Flavonoids are a broad class of polyphenolic secondary metabolites abundant in plants and in a variety of common foods such as apples, onions, tea and red wine. Many clinically successful anticancer drugs were themselves either naturally occurring molecules or have been developed from their synthetic analogs.

Article titled "A general and facile one-pot process of isothiocyanates from amines under aqueous conditions" by N Sun et al. published in *Beilstein J Org Chem.*, 2012, 8, 61-70 reports a general and facile one-pot protocol for the preparation of a broad range of alkyl and aryl isothiocyanates from their corresponding primary amines under aqueous conditions.

Article titled "Studies in the chemistry of some new 1,2,4-thiadiazolidine by oxidative cyclisation" by D T Tayade et al. published in *International Journal of Chemistry*, 2010, 2 (2), pp 40-43 reports a novel series of Hector's bases (1, 2, 4-thiadiazolidine). The 1-substituted-3-formamidinothiocarbamides (1a-f) and 1,3-bis(N-substituted-thioamido) guanidines (1g-l) are oxidatively cyclized by using aqueous bromine as oxidizing agent in chloroform medium to synthesize new series of Hectors bases, viz; 3-imino-5-substituted imino-1,2,4-thiadiazolidine (2a-f) and 3-substituted thioamidoimino-5-substitutedimino-1,2,4-thiadiazolidine (2g-l), respectively.

Article titled "Synthesis and Antimicrobial Activity of 3-Amino-5-aryl/alkylimino-1,2,4-thiadiazolines" by S V Gandhe et al. published in *Asian J. Chem.*, 2008, 20(1), pp 32-36 reports 3-amino-5-aryl/alkyl imino-1,2,4-thiadiazolines (IV) synthesized by the oxidative cyclization of 1-amidino-3-aryl/alkyl thiocarbamides (II) with iodine followed by basification.

PCT application no. 2007026251 disclosed a method for treating Multiple Myeloma, FGFR3+ myeloma, especially relapsed or refractory multiple myeloma (4/14) expressing FGFR3, comprising administering a dual C-KIT/FGFR3 inhibitor to a human in need of such treatment, wherein said inhibitor is selected from the group consisting of 2-amino-arylthiazoles and 2-aminoaryloxazoles of formula I:

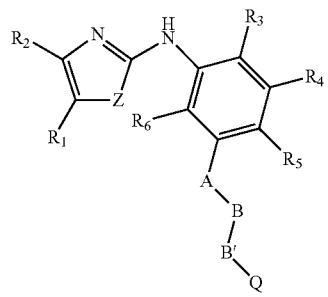

wherein, Z is oxygen or sulfur.

A and B' is one of the following: i) (R7)N(CH$_2$)$_n$ where n is 0 or 1 ii) O(CH$_2$)$_n$ where n is 0 or 1 iii) S(CH$_2$)$_n$ where n is 0 or 1 iv) (CH$_2$)$_n$ where n is 0, 1 or 2 v) C(O)(CH$_2$)$_n$ where n is 0 or 1 or when A and B$^1$ each are a nitrogen, they may be taken together to form a bivalent radical of formula: —(CH$_2$)$_s$—X1-(CH$_2$)$_t$— (a) where s and t each independently is 1 or 2 and X1 being O, S, NR10, N[C(=O)R10] or (CH$_2$)$_n$ where n is 0 or 1, and wherein each hydrogen in said formula (a) may be substituted with halo or alkyl, B is one of the following: i) (R7)N ii) Oxygen iii) S(O)$_n$ where n is 0, 1 or 2 iv) CH(R7)(R8) v) C=δ, where δ is oxygen, sulfur, NH or N—CN vi) C(R7)=C(R8) vii) N=C (R7), R7 and R8 each independently are hydrogen, alkyl, C$_{2-6}$alkenyl, C$_{2-6}$ alkynyl, C$_3$-C$_7$cycloalkyl, R1 and R2 is selected from: i) hydrogen, halogen (selected from F, Cl, Br or I)$_5$ or ii) an alkyl$^1$ group defined as a linear, branched or cycloalkyl group containing from 1 to 10 carbon atoms and optionally substituted with one or more heteroatoms such as halogen (selected from F, Cl, Br or I), oxygen, and nitrogen (the latter optionally in the form of a pendant basic nitrogen functionality); as well as trifluoromethyl, carboxyl, cyano, nitro, formyl;

R3, R4, R5 and R6 each independently are selected from hydrogen, halogen and wherein Q is selected from: i) Alkyl$^1$ ii) Aryl$^1$ iii) Heteroaryl$^1$ as defined above.

Article titled "Synthesis and antimicrobial evaluation of some novel 2-aminothiazole derivatives of 4-hydroxy-chromene-2-one" by N Vukovic et al. published in *Arch. Pharm. Chem. Life Sci.*, 2008, 341, pp 491-496 reports synthesis of 2-aminothiazole derivatives of 4-hydroxy-chromene-2-one (2c-10c).

The effectiveness of most anticancer agents is greatly reduced because of their high toxicity and the nature of the illness. It is believed that the problem of high toxicity of the anticancer agents can be circumvented by chemical modifications of those structures in such a way that they act more specifically on tumor cells without increasing systemic toxicity.

The patients with metastatic cancers such as lung, colorectal, pancreatic or head and neck who initially benefited from epidermal growth factor receptor (EGFR)-targeted therapies eventually develop resistance due to EGFR mutation. Also, it will be difficult to understand the complexity of resistance mechanisms and hence becomes a challenge to the doctor to control the tumors that are resistant to EGFR inhibitors.

The research in this field is therefore mainly directed to the synthesis of anticancer agents which would possess high antineoplastic activity, low systemic toxicity and low mutagenicity on normal cells. Accordingly, inventors of present invention had developed novel flavone based EGFR inhibitors for the treatment of abnormal cell growth in mammals.

OBJECTIVE OF THE INVENTION

The main objective of the present invention is to provide a novel flavone based EGFR inhibitor compound of formula (I);

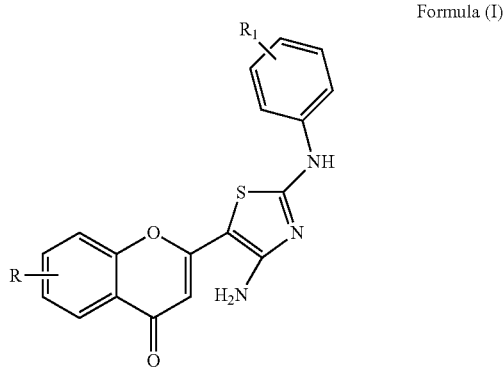

Formula (I)

wherein, R is selected from hydrogen, alkyl, nitro, halogens such as chlorine, bromine, fluorine and iodine;
$R_1$=hydrogen, alkyl, alkoxy, aryl, nitro, halogens such as chlorine, bromine, fluorine and iodine, trifluoromethyl, thioalkyl, trifluromethoxy, trialkylsilyl.

Another objective of the present invention is to provide a process for preparation of compounds of formula (I) from substituted 1-phenyl-3-formamidinothiocarbamide.

Still another objective of the present invention is to provide a method for treating abnormal cell growth in mammals by administering said compound of formula (I) and a pharmaceutical composition for treating such disorders that contain the compound of formula (I).

SUMMARY OF THE INVENTION

Accordingly, the present invention provides a novel flavone based EGFR inhibitor compound of formula (I);

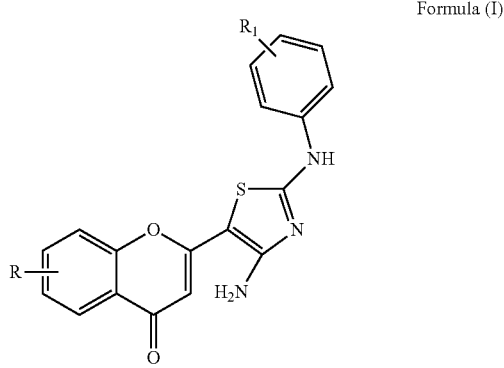

Formula (I)

wherein, R is selected from hydrogen, alkyl, nitro, halogens such as chlorine, bromine, fluorine and iodine;
$R_1$=hydrogen, alkyl, alkoxy, aryl, nitro, halogens such as chlorine, bromine, fluorine and iodine, trifluoromethyl, thioalkyl, trifluromethoxy, trialkylsilyl.

In another embodiment, the present invention provides a process for the preparation of compounds of formula (I), wherein said process comprising the steps of:
a) reacting a mixture of substituted phenyl amine in water with carbon disulfide in presence of suitable base followed by reaction with cyanuric chloride to afford substituted N-Phenyl isothiocynate;
b) reacting N-Phenyl isothiocynate with guanidine in carbon tetrachloride by refluxing the mixture for the period in the range of 2-4 hrs to afford substituted 1-phenyl-3-formamidinothiocarbamide (intermediate 1);
c) refluxing the reaction mixture of substituted 2-hydroxy acetophenone and chloroacetyl chloride in dimethyl formamide in presence of sodium chloro acetate at a temperature in the range of 185 to 195° C. to for a period in the range of 5 to 6 hr to afford 2-Chloromethyl-4-H-Chromen-4-one derivatives (intermediate 2);
d) refluxing the solution containing compound of step (b) and compound of step (c) in methanol for a period in the range 4 to 6 hrs at a temperature in the range of 50 to 70° C. to afford compound of formula (I).

In preferred embodiment, said substituted phenyl amine compound is selected from phenyl amine, 4-methoxy phenyl amine, 4-nitro phenyl amine, 2-nitro phenyl amine, 4-Chloro phenyl amine, 3-(trifluoromethyl) benzenamine, 3,5-bis (trifluoromethyl) benzenamine, 4-(trifluoromethoxy) benzenamine, 2,4,6-trimethylbenzenamine and 4-bromo-2-fluorobenzenamine.

In another preferred embodiment, said substituted N-Phenyl Isothiocynate compound is selected from phenyl isothiocynate, 4-methoxy phenyl isothiocynate, 4-nitro phenyl isothiocynate, 2-nitro phenyl isothiocynate, 4-Chloro phenyl isothiocynate, 2-isothiocyanato-1,3,5-trimethylbenzene and 4-bromo-2-fluoro-1-isothiocyanatobenzene.

In yet another preferred embodiment, said substituted 1-phenyl-3-formamidinothiocarbamide compound is selected from 1-phenyl-3-formamidinothiocarbamide, 4-Methoxy Phenyl-3-formamidinothiocarbamide, 4-Nitro Phenyl-3-formamidinothiocarbamide, 2-Nitro Phenyl-3-formamidinothiocarbamide, 4-Chloro Phenyl-3-formamidinothiocarbamide, 2,4,6-trimethyl Phenyl-3-formamidinothiocarbamide and 2-Fluro,4-Bromo phenyl-3 formamidinothiocarbamide.

In still another preferred embodiment, said substituted 2-hydroxy acetophenone in step (c) is selected from 1-(2-hydroxyphenyl) ethanone, 1-(2-hydroxy-4-methylphenyl) ethanone, 1-(2,4-dihydroxyphenyl)ethanone, 1-(4-chloro-2-hydroxyphenyl)ethanone, 1-(4-fluoro-2-hydroxyphenyl) ethanone.

In yet still another preferred embodiment, said compound named intermediate 2 in step (c) is selected from 2-Chloromethyl-4-H-Chromen-4-one, 2-(Chloromethyl)-7-Hydroxy-4-H-Chromen-4-one and 2-(Chloromethyl)-6-Methoxy-4-H-Chromen-4-one.

In still another embodiment, the present invention provides a method of treating abnormal cell growth in mammals by administering the compounds of formula (I) and a pharmaceutical composition for treating such disorders that contain the compounds of formula (I).

In an embodiment, the present invention provides the method of treating abnormal cell growth in mammals by administering the compounds of formula (I), wherein said subject is human.

DETAILED DESCRIPTION OF THE INVENTION

Figure 1:
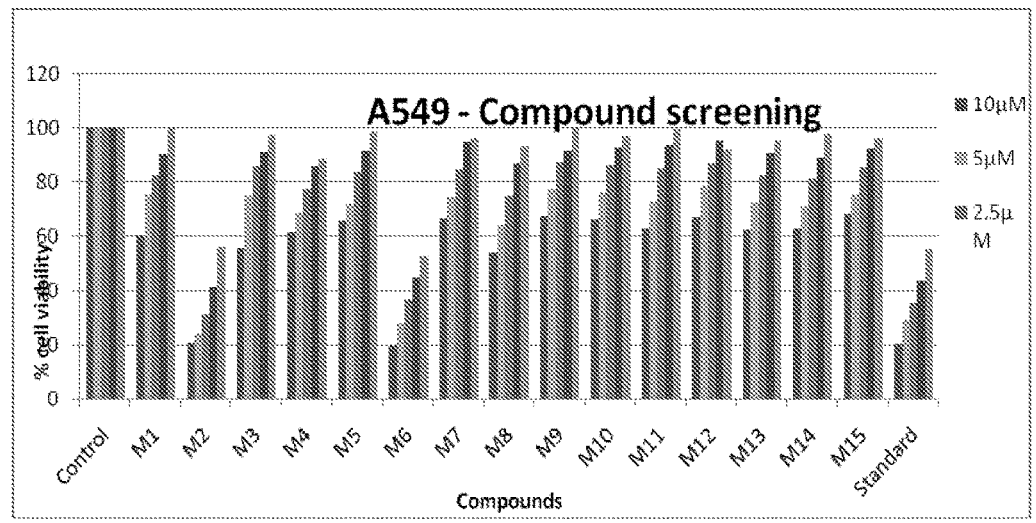
FIG. 1: In-Vitro Anticancer activity against A549 Cell line (Lung Cancer Cell line) (adenocarcinomic human alveolar basal epithelial cells) (Standard is gefitinib)
Figure 2:
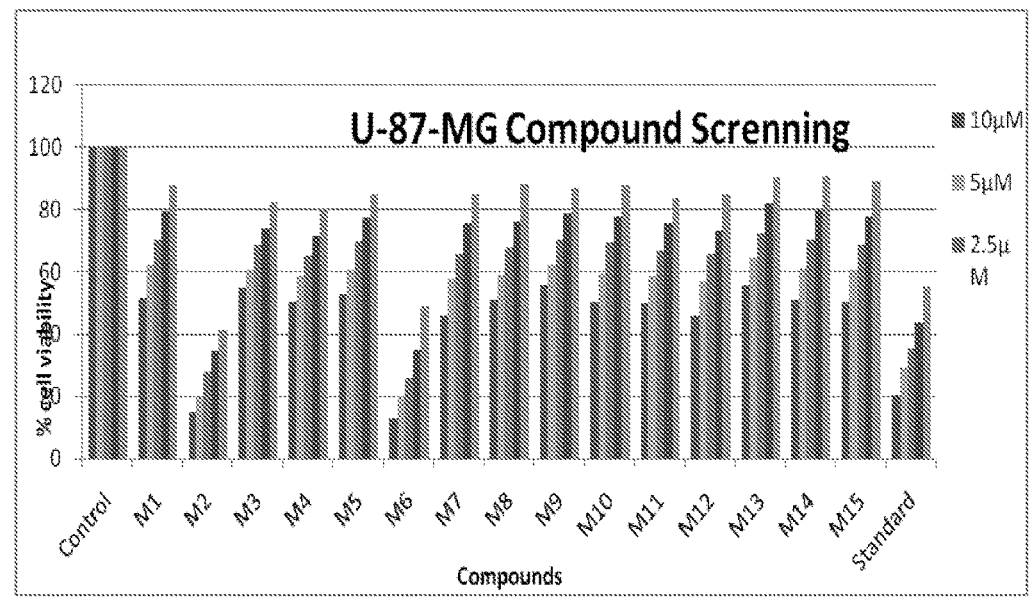
FIG. 2: In-Vitro Anticancer activity against U87MG Cell line (glioblastoma cell line) (Standard is gefitinib)

The invention will now be described in detail in connection with certain preferred and optional embodiments, so that various aspects thereof may be more fully understood and appreciated.

Unless specified otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described. To describe the invention, certain terms are defined herein specifically as follows.

Unless stated to the contrary, any of the words "including," "includes," "comprising," and "comprises" mean "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth in the appended claims.

In the view of above, the present invention provides a novel flavone based EGFR inhibitor compound of formula (I);

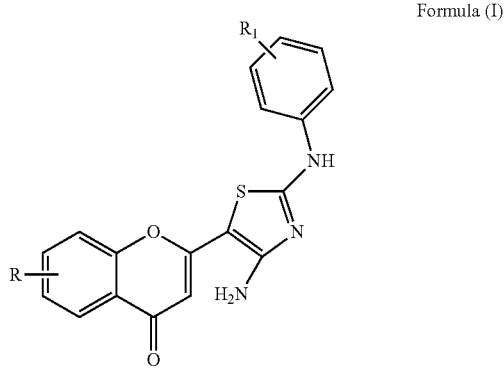

Formula (I)

wherein, R is selected from hydrogen, alkyl, nitro, halogens such as chlorine, bromine, fluorine and iodine;

$R_1$=hydrogen, alkyl, alkoxy, aryl, nitro, halogens such as chlorine, bromine, fluorine and iodine, trifluoromethyl, thioalkyl, trifluromethoxy, Trialkylsilyl.

In preferred embodiment, the present invention provides a novel flavone based EGFR inhibitor compound of formula (I);

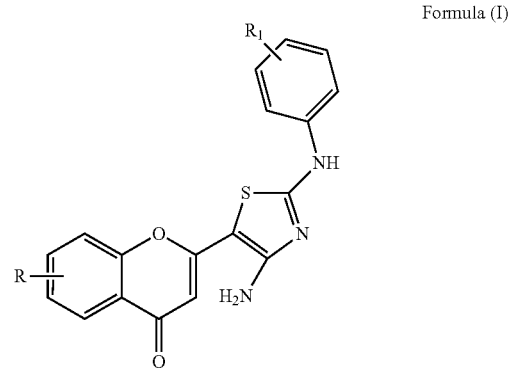

Formula (I)

Wherein, R=—H, 3-$CH_3$, 4-$NO_2$, 4-Cl, 2-$CH_3$, 4-$CH_3$, 4-Br, 4-F;

$R_1$=—H, -4-$OCH_3$, -4-$NO_2$-2-$NO_2$, -4-Cl, -2,4,6-$CH_3$, -4-$CH_3$, -2-F,4-Br, -4-$CF_3$, -4-S—$CH_3$, -4-Cl, -3-$CF_3$, -3-S—$CH_3$, -3,5-$CF_3$, -2-S—$CH_3$, -3-$CF_3$-4-$OCH_3$, —Si—$(CH_3)_3$, —Si—$(C_2H_5)_3$, $(CH_3)_2$—Si—$C_2H_5$.

In another preferred embodiment, the compound of formula (I) is selected from;
a. 2-(4-amino-2-(phenylamino) thiazol-5-yl)-4H-chromen-4-one (S1-M1),
b. 2-(2-(p-tolylamino)-4-aminothiazol-5-yl)-7-hydroxy-4H-chromen-4-one (S1-M2),
c. 2-(2-(o-tolylamino)-4-aminothiazol-5-yl)-7-hydroxy-4H-chromen-4-one (S1-M3),
d. 2-(2-(2,6-dimethylphenylamino)-4-aminothiazol-5-yl)-7-hydroxy-4H-chromen-4-one (S1-M4),
e. 2-(2-(2,6-dichlorophenylamino)-4-aminothiazol-5-yl)-7-hydroxy-4H-chromen-4-one (S1-M5),
f. 2-(2-(4-methoxyphenylamino)-4-aminothiazol-5-yl)-7-hydroxy-4H-chromen-4-one (S1-M6),
g. 2-(2-(2-methoxyphenylamino)-4-aminothiazol-5-yl)-7-hydroxy-4H-chromen-4-one (S1-M7),
h. 2-(4-amino-2-(phenylamino) thiazol-5-yl)-7-hydroxy-4H-chromen-4-one (S1-M8),
i. 2-(2-(p-tolylamino)-4-aminothiazol-5-yl)-4H-chromen-4-one (S1-M9),
j. 2-(2-(p-tolylamino)-4-aminothiazol-5-yl)-6-methoxy-4H-chromen-4-one (S1-M10),
k. 2-(2-(o-tolylamino)-4-aminothiazol-5-yl)-6-methoxy-4H-chromen-4-one (S1-M11),
l. 2-(2-(2,6-dimethylphenylamino)-4-aminothiazol-5-yl)-6-methoxy-4H-chromen-4-one (S1-M12),
m. 2-(2-(2,6-dichlorophenylamino)-4-aminothiazol-5-yl)-6-methoxy-4H-chromen-4-one (S1-M13),
n. 2-(2-(4-methoxyphenylamino)-4-aminothiazol-5-yl)-7-methoxy-4H-chromen-4-one (S1-M14),
o. 2-(2-(2-methoxyphenylamino)-4-aminothiazol-5-yl)-7-methoxy-4H-chromen-4-one (S1-M15).

In another embodiment, the present invention provides a process for the synthesis of compounds of formula (I) comprising the steps of:
a) reacting a mixture of substituted phenyl amine in water with carbon disulfide in presence of suitable base followed by reaction with cyanuric chloride to afford substituted N-Phenyl isothiocynate;
b) reacting N-Phenyl isothiocynate with guanidine in carbon tetrachloride by refluxing the mixture for the period in the range of 2-4 hrs to afford substituted 1-phenyl-3-formamidinothiocarbamide (intermediate 1);

c) refluxing the reaction mixture of substituted 2-hydroxy acetophenone and chloroacetyl chloride in dimethyl formamide in presence of sodium chloro acetate at a temperature in the range of 185 to 195° C. to for a period in the range of 5 to 6 hr to afford 2-Chloromethyl-4-H-Chromen-4-one or its derivatives (intermediate 2);

d) refluxing the solution containing compound of step (b) and compound of step (c) in methanol for a period in the range 4 to 6 hrs at a temperature in the range of 50 to 70° C. to afford compound of formula (I).

In preferred embodiment, said substituted phenyl amine compound in step (a) is selected from phenyl amine, 4-methoxy phenyl amine, 4-nitro phenyl amine, 2-nitro phenyl amine, 4-Chloro phenyl amine, 3-(trifluoromethyl) benzenamine, 3,5-bis (trifluoromethyl) benzenamine, 4-(trifluoromethoxy) benzenamine, 2,4,6-trimethylbenzenamine and 4-bromo-2-fluorobenzenamine.

In another preferred embodiment, said substituted N-Phenyl Isothiocynate compound in step (a) is selected from phenyl isothiocynate, 4-methoxy phenyl isothiocynate, 4-nitro phenyl isothiocynate, 2-nitro phenyl isothiocynate, 4-Chloro phenyl isothiocynate, 2-isothiocyanato-1,3,5-trimethylbenzene and 4-bromo-2-fluoro-1-isothiocyanatobenzene.

In yet another preferred embodiment, said substituted 1-phenyl-3-formamidinothiocarbamide compound in step (b) is selected from 1-phenyl-3-formamidinothiocarbamide, 4-Methoxy Phenyl-3-formamidinothiocarbamide, 4-Nitro Phenyl-3-formamidinothiocarbamide, 2-Nitro Phenyl-3-formamidinothiocarbamide, 4-Chloro Phenyl-3-formamidinothiocarbamide, 2,4,6-trimethyl Phenyl-3-formamidinothiocarbamide and 2-Fluro,4-Bromo phenyl-3 formamidinothiocarbamide.

In still another preferred embodiment, said substituted 2-hydroxy acetophenone compound in step (c) is selected from 1-(2-hydroxyphenyl) ethanone, 1-(2-hydroxy-4-methylphenyl)ethanone, 1-(2,4-dihydroxyphenyl)ethanone, 1-(4-chloro-2-hydroxyphenyl)ethanone, 1-(4-fluoro-2-hydroxyphenyl)ethanone.

In yet another preferred embodiment, said compound named intermediate 2 in step (c) is selected from 2-Chloromethyl-4-H-Chromen-4-one, 2-(Chloromethyl)-7-Hydroxy-4-H-Chromen-4-one and 2-(Chloromethyl)-6-Methoxy-4-H-Chromen-4-one.

The base as used in step (a) is potassium carbonate.

The synthesis may be conveniently carried out from ambient to reflux temperature of the solvent used in the specific reaction step. The solvents that can be used in the synthesis may be selected from the group ranging from polar to non-polar solvents such as water, C1 to C6 alcohols, hydrocarbons, halogenated hydrocarbons and the like.

The compounds of the invention may comprise one or more chiral centers and hence encompasses its racemates, cis- or trans-isomeric forms and its enantiomers/diastereomers.

In yet another embodiment, the invention provides process for synthesis of compounds of formula I, as per the scheme 1 shown below.

Scheme 1: synthesis of compound of formula 1

General Scheme for Synthesis of Flavone derivatives:

Step: 1

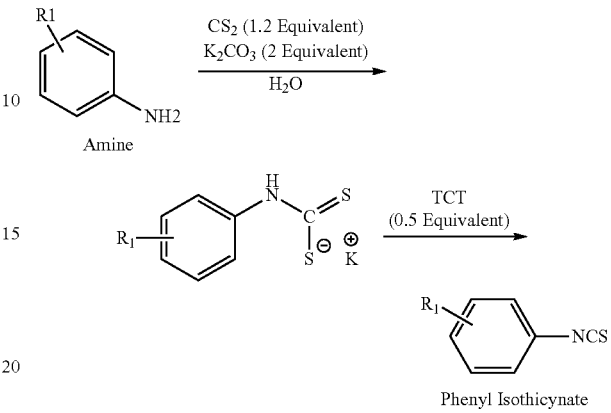

Phenyl Isothicynate

Step 2:

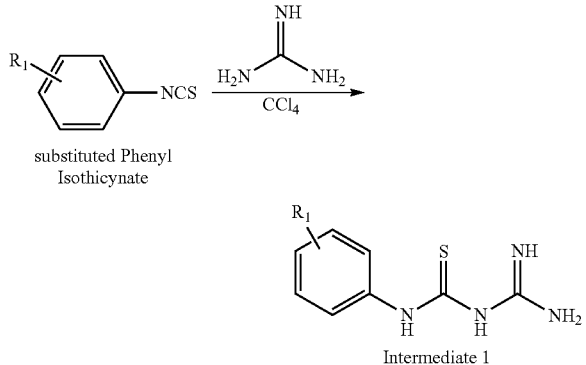

Intermediate 1

Step 3:

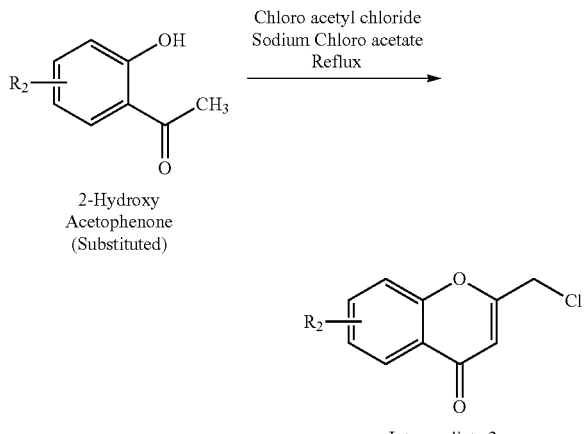

Intermediate 2

Step 4:

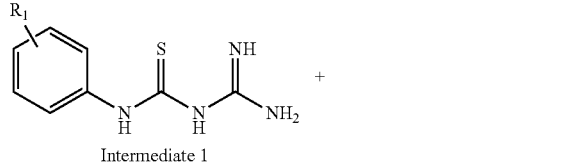

Intermediate 1

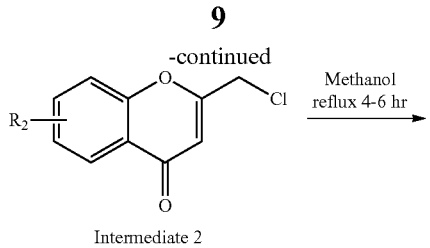

Intermediate 2

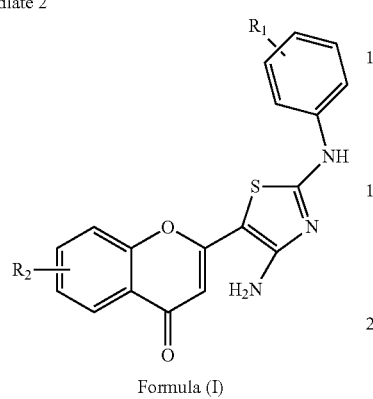

Formula (I)

The compounds of the invention described have been preliminarily screened for their efficacy in treating cancer and related diseases by an in vitro cell proliferation assay against A549 Cell line and U87MG Cell line as exemplified herein below. Other methods will also be apparent to those of ordinary skill in the art.

In one embodiment, the present invention provides a pharmaceutical composition containing an effective amount of compound of formula (I) and at least one pharmaceutical acceptable carrier.

"An effective amount" as mentioned above refers to an amount of a compound of formula (I) that is required to confer a therapeutic effect on the treated subject. Effective doses will vary, as recognized by those skilled in the art, depending on the types of diseases treated, routes of administration, usage of excipients, and the possibility of co-usage with other therapeutic treatments.

The methods of administration of the compounds of the invention include parenteral, oral, nasal, topical, rectal, or buccal administration.

A composition for oral and injectable administration can be a dosage form including capsules, tablets, emulsions and aqueous suspensions, dispersions, and solutions. A composition having one or more active compounds of formula (I) according to the invention can also is administered in the form of suppositories for rectal administration.

The pharmaceutical excipients that may be suitable to administer the compounds of the invention includes binders, fillers, lubricants, disintigrants, oil based and wax based excipients, diluents etc. If desired, certain sweetening, flavoring, or coloring agents can be added to the formulation.

In yet another embodiment, the present invention provides a method for treating abnormal cell growth in mammals comprising administering to the subject an effective amount of compound of formula (I).

"An effective amount" refers herein to an amount of a compound of formula (I) that is required to confer a therapeutic effect on the treated subject. Abnormal cell growth is normally developed in the case of cancers and related diseases. Effective doses will vary, as recognized by those skilled in the art, depending on the types of diseases treated, routes of administration, usage of excipients, and the possibility of co-usage with other therapeutic treatments.

In still another embodiment, the present invention provides compounds of formula (I) for use in the treatment of cancer and related diseases in a subject to confer a therapeutic effect on the treated subject.

The cancer and related disease include the cancers that originated from human organs selected from the group consisting of breast; cervical; colon; lung; head and neck cancer; brain; skin; bone and the like.

EXAMPLES

Following examples are given by way of illustration therefore should not be construed to limit the scope of the invention.

Example 1: Preparation of N-Phenyl Isothiocynate[1]

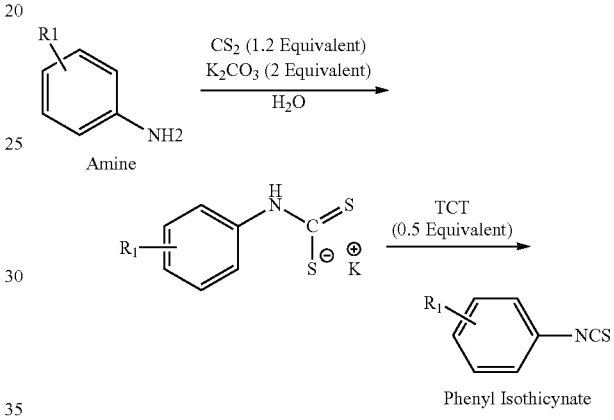

Phenyl Isothicynate

To a mixture of amine (20 mmol) and $K_2CO_3$ (5.52 g, 40 mmol) in 20 mL of water 1.82 g of CS2 (24 mmol) was added drop wise in a period of 20-30 min at room temperature. After the addition was complete, the mixture was stirred for several hours until complete conversion. Then, the reaction mixture was cooled to 0° C. and a solution of 1.85 g of TCT (10 mmol) in 15 mL of $CH_2Cl_2$ was added drop wise. After the addition was complete, the mixture was stirred for another 0.5 h to finish the reaction. The reaction mixture was then basified to pH>11 with 6 N NaOH to obtain a clear solution. The organic layer was separated and the aqueous phase was extracted with $CH_2Cl_2$ (2×10 mL). The combined organic layers were dried over anhydrous $Na_2SO_4$, filtered and the solvent was removed.

TABLE 1

| No. | Compound | $R_1$ | Nature | % Yield |
|---|---|---|---|---|
| 1 | Phenyl Isothiocynate | —H | colorless oil | 98 |
| 2 | 4-Methoxy Phenyl Isothiocynate | -4-$OCH_3$ | colorless oil | 86 |
| 3 | 4-Methyl Phenyl Isothiocynate | -4-$CH_3$ | colorless oil | 92 |
| 4 | 2-Methyl Phenyl Isothiocynate | -2-$CH_3$ | colorless oil | 92 |
| 5 | 2-Methoxy Phenyl Isothiocynate | -2-$OCH_3$ | white solid | 82 |
| 6 | 2,6-Dimethyl Phenyl Isothiocynate | -2,6-$CH_3$ | white solid | 80 |
| 7 | 2,6-Dichloro Phenyl Isothiocynate | -2,6-Cl | Cream Solid | 70 |

Example 2: Preparation of Intermediate 1: 1-phenyl-3-formamidinothiocarbamide[2]: General Reaction[2]

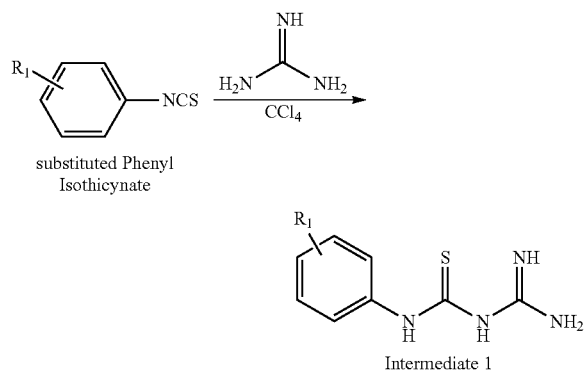

substituted Phenyl Isothicynate

Intermediate 1

A mixture of guanidine (0.01 M) and phenyl isothiocynate (0.01 M) and carbon tetrachloride (50 mL) was refluxed on a water bath for 2 hours. During boiling, the reaction mixture containing the suspended guanidine went into solution and after 1 hour yellowish, needle-shaped crystals gradually separated out. The reaction mixture was then again refluxed for 1 hour then filtered while hot. The new product was dried at room temperature and recrystallized from aqueous ethanol.

TABLE 2

| No. | Compound | $R_1$ | % Yield |
| --- | --- | --- | --- |
| 1 | 1-phenyl-3-formamidinothiocarbamide | —H | 72 |
| 2 | 4-Methoxy Phenyl-3-formamidinothiocarbamide | -4-OCH$_3$ | 78 |
| 3 | 4-Methyl Phenyl-3-formamidinothiocarbamide | -4-CH$_3$ | 65 |
| 4 | 2-Methyl Phenyl-3-formamidinothiocarbamide | -2-CH$_3$ | 80 |
| 5 | 2-Methoxy Phenyl-3-formamidinothiocarbamide | -2-OCH$_3$ | 82 |
| 6 | 2,6-Dimethyl Phenyl-3-formamidinothiocarbamide | -2,6-CH$_3$ | 86 |
| 7 | 2,6-Dichloro PhenyL-3-formamidinothiocarbamide | -2,6-Cl | 74 |

Example 3: Preparation of 2-Chloromethyl-4-H-Chromen-4-one Derivatives[3,4]

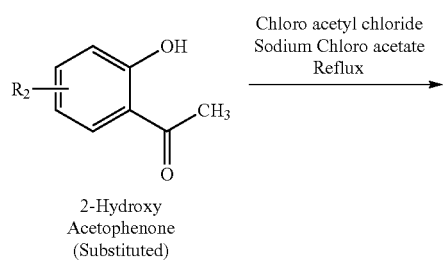

2-Hydroxy Acetophenone (Substituted)

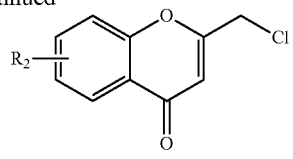

Intermediate 2

The substituted 2-hydroxy acetophenone (0.01M) and chloroacetyl chloride (0.01M) in presence of sodium chloro acetate in dimethyl formamide refluxed at 190° C. for 5 to 6 hrs yields 2-Chloromethyl-4-H-Chromen-4-one derivatives in 50 to 65%.

TABLE 3

| No. | Compound | $R_1$ | % Yield |
| --- | --- | --- | --- |
| 1 | 2-Chloromethyl-4-H-Chromen-4-one | —H | 50 |
| 2 | 2-(Chloromethyl)-7-Hydroxy-4-H-Chromen-4-one | -7-OH | 59 |
| 3 | 2-(Chloromethyl)-6-Methoxy-4-H-Chromen-4-one | -6-OCH$_3$ | 65 |

Example 4: Preparation of Compounds of Formula (I)

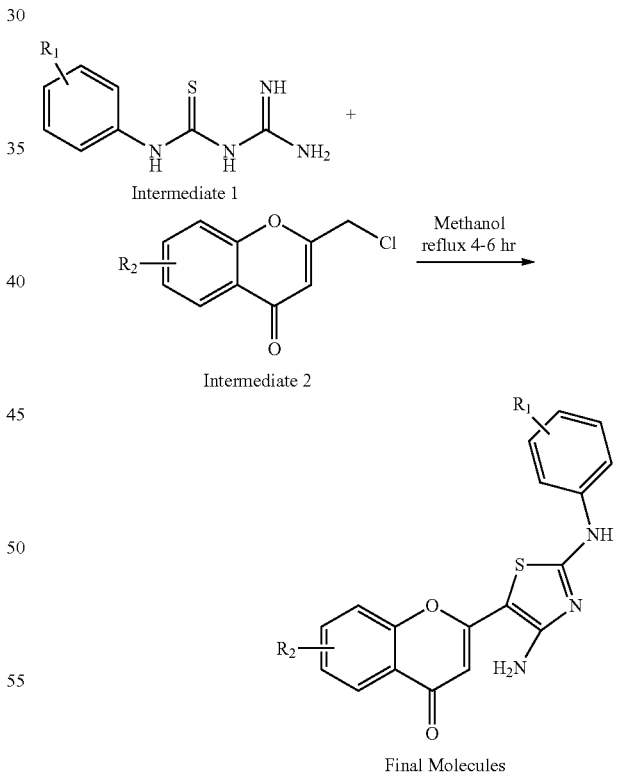

Final Molecules

Substituted phenyl-3-formamidinothiocarbamide (0.01 M) and different substituted 2-Chloromethyl-4-H-Chromen-4-one (0.01 M) were refluxed for 4-6 hours in methanol at 60° C. Reaction was monitored by TLC, after completion of reaction Solvent was evaporated by rotary evaporator, and then column was carried out by using silica 60-120, Mobile phase Ethyl acetate:Pet ether (5:5).

TABLE 4

| Sr. No. | Compound Code | Molecular Formula | Molecular Weight | Log P | Yield (%) | M.P. (° C.) |
|---|---|---|---|---|---|---|
| 1 | S1-M1 | $C_{18}H_{13}N_3O_2S$ | 335.07 | 3.20 | 70.20 | 232-234 |
| 2 | S1-M2 | $C_{19}H_{15}N_3O_3S$ | 365.08 | 1.90 | 72.14 | 244-246 |
| 3 | S1-M3 | $C_{19}H_{15}N_3O_3S$ | 365.08 | 2.01 | 68.30 | 268-270 |
| 4 | S1-M4 | $C_{20}H_{17}N_3O_3S$ | 379.1 | 3.42 | 69.80 | 224-226 |
| 5 | S1-M5 | $C_{18}H_{11}Cl_2N_3O_3S$ | 418.99 | 3.02 | 54.30 | 260-262 |
| 6 | S1-M6 | $C_{19}H_{15}N_3O_4S$ | 381.08 | 1.92 | 65.50 | 220-222 |
| 7 | S1-M7 | $C_{19}H_{15}N_3O_4S$ | 381.08 | 2.11 | 66.70 | 210-212 |
| 8 | S1-M8 | $C_{18}H_{13}N_3O_3S$ | 351.07 | 3.32 | 77.30 | 218-220 |
| 9 | S1-M9 | $C_{19}H_{15}N_3O_2S$ | 349.09 | 1.90 | 78.20 | 200-202 |
| 10 | S1-M10 | $C_{20}H_{17}N_3O_3S$ | 379.1 | 3.99 | 71.10 | 280-282 |
| 11 | S1-M11 | $C_{20}H_{17}N_3O_3S$ | 379.1 | 2.11 | 68.10 | 288-290 |
| 12 | S1-M12 | $C_{21}H_{19}N_3O_3S$ | 393.11 | 2.70 | 65.11 | 228-230 |
| 13 | S1-M13 | $C_{19}H_{13}Cl_2N_3O_3S$ | 433.01 | 2.18 | 54.22 | 260-262 |
| 14 | S1-M14 | $C_{20}H_{17}N_3O_4S$ | 395.09 | 2.60 | 65.32 | 220-222 |
| 15 | S1-M15 | $C_{20}H_{17}N_3O_4S$ | 395.09 | 2.50 | 66.88 | 210-212 |

Example 5: Cell Proliferation Assays

Each cell line was plated in 96-well microtiter plates (10,000 cells per well), and serial dilutions of indicated compounds were added. At the end of the incubation period (72 h at 37° C.), cell viability was determined by a tetrazolium dye, MTT (3-(4,5-dimethylthiazol-2-yl)-2,5-diphenyl tetrazolium bromide) (Promega, USA). The formazan crystals were dissolved in DMSO, and the absorbance at 600 nm was recorded using an ELISA plate reader. IC50 values were calculated using nonlinear regression and defined as the concentration needed for a 50% reduction in absorbance of treated versus untreated control cells.

In-Vitro Anticancer Activity Against A549 Cell Line (Lung Cancer Cell Line) (Adenocarcinomic Human Alveolar Basal Epithelial Cells)

| | % cell viability | | | | |
|---|---|---|---|---|---|
| | 10 µM | 5 µM | 2.5 µM | 0.1 µM | 0.01 µM |
| Control | 100 | 100 | 100 | 100 | 100 |
| M1 | 60.4651 | 75.4651 | 82.4651 | 90.4651 | 99.9744 |
| M2 | 20.9448 | 24.1235 | 31.1210 | 41.0943 | 56.0943 |
| M3 | 55.8410 | 74.8410 | 85.8410 | 91.3697 | 97.6429 |
| M4 | 61.5611 | 68.5611 | 77.5611 | 85.7952 | 88.6071 |
| M5 | 65.9487 | 71.9487 | 83.9487 | 91.5791 | 98.8393 |
| M6 | 19.4286 | 27.8703 | 36.6810 | 45.0516 | 53.0586 |
| M7 | 66.7909 | 74.7909 | 84.7909 | 94.9283 | 96.0714 |
| M8 | 54.0435 | 64.0435 | 75.0435 | 87.1263 | 93.3214 |
| M9 | 67.3118 | 77.3118 | 87.3118 | 91.8430 | 99.9887 |
| M10 | 66.3915 | 76.3915 | 86.3915 | 93.0148 | 96.9286 |
| M11 | 62.8332 | 72.8332 | 84.8332 | 93.6860 | 99.7857 |
| M12 | 66.9492 | 78.9492 | 86.9492 | 95.3561 | 92.1429 |
| M13 | 62.6358 | 72.6358 | 82.6358 | 90.9272 | 95.4107 |
| M14 | 63.1210 | 71.1210 | 81.1210 | 89.1126 | 98.0357 |
| M15 | 68.3067 | 75.3067 | 85.3067 | 92.6507 | 96.1071 |
| Gefitinib | 20.3067 | 29.3067 | 35.3067 | 43.6507 | 55.2143 |

In-Vitro Anticancer Activity Against U87MG Cell Line (Glioblastoma Cell Line)

| | % cell viability | | | | |
|---|---|---|---|---|---|
| | 10 µM | 5 µM | 2.5 µM | 0.1 µM | 0.01 µM |
| Control | 100 | 100 | 100 | 100 | 100 |
| M1 | 51.4651 | 62.4651 | 70.4651 | 79.4651 | 87.9744 |
| M2 | 14.9447 | 19.5976 | 28.1210 | 34.3781 | 41.1378 |
| M3 | 54.8410 | 60.8410 | 68.8410 | 74.3697 | 82.6429 |
| M4 | 50.5611 | 58.5611 | 65.5611 | 71.7952 | 80.6071 |
| M5 | 52.9487 | 60.9487 | 69.9487 | 77.5791 | 84.8393 |
| M6 | 12.8571 | 19.8717 | 25.8168 | 35.1561 | 48.7083 |
| M7 | 45.7909 | 57.7909 | 65.7909 | 75.9283 | 85.0714 |
| M8 | 51.4350 | 59.0435 | 68.0435 | 76.1263 | 88.3214 |
| M9 | 55.6358 | 62.3118 | 70.3118 | 78.8430 | 86.9887 |
| M10 | 50.3915 | 59.3915 | 69.3915 | 78.0148 | 87.9286 |
| M11 | 49.8332 | 58.8332 | 67.2404 | 75.6860 | 83.7857 |
| M12 | 45.7987 | 56.9492 | 65.9492 | 73.3561 | 85.1429 |
| M13 | 55.9492 | 64.6358 | 72.3581 | 81.9272 | 90.4107 |
| M14 | 51.1210 | 61.2621 | 70.6213 | 80.1126 | 91.0357 |
| M15 | 50.3067 | 60.6748 | 68.7485 | 77.9477 | 89.1071 |
| Gefitinib | 20.3067 | 29.3067 | 35.3067 | 43.6507 | 55.2143 |

ADVANTAGES OF THE INVENTION

New anti cancer compounds provided
The compounds possess good anti cancer efficacy
The process of synthesis is simple

The invention claimed is:
1. A compound of formula (I)

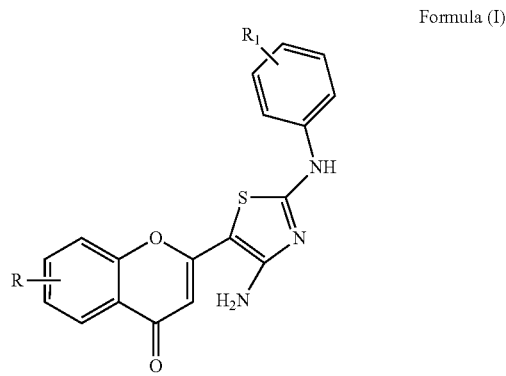

Formula (I)

wherein, R is selected from hydrogen, alkyl, nitro and halogens selected from the group consisting of chlorine, bromine, fluorine and iodine;

$R_1$=hydrogen, alkyl, alkoxy, aryl, nitro, trifluoromethyl, thioalkyl, trifluoromethoxy, trialkylsilyl and halogens selected from the group consisting of chlorine, bromine, fluorine and iodine.

2. The compound as claimed in claim 1, wherein said compounds are selected from
  2-(4-amino-2-(phenylamino) thiazol-5-yl)-4H-chromen-4-one (S1-M1),
  2-(2-(p-tolylamino)-4-aminothiazol-5-yl)-7-hydroxy-4H-chromen-4-one (S1-M2),
  2-(2-(o-tolylamino)-4-aminothiazol-5-yl)-7-hydroxy-4H-chromen-4-one (S1-M3),
  2-(2-(2,6-dimethylphenylamino)-4-aminothiazol-5-yl)-7-hydroxy-4H-chromen-4-one (S1-M4),
  2-(2-(2,6-dichlorophenylamino)-4-aminothiazol-5-yl)-7-hydroxy-4H-chromen-4-one (S1-M5),
  2-(2-(4-methoxyphenylamino)-4-aminothiazol-5-yl)-7-hydroxy-4H-chromen-4-one (S1-M6),
  2-(2-(2-methoxyphenylamino)-4-aminothiazol-5-yl)-7-hydroxy-4H-chromen-4-one (S1-M7), 2-(4-amino-2-(phenylamino) thiazol-5-yl)-7-hydroxy-4H-chromen-4-one (S1-M8),
2-(2-(p-tolylamino)-4-aminothiazol-5-yl)-4H-chromen-4-one (S1-M9),
2-(2-(p-tolylamino)-4-aminothiazol-5-yl)-6-methoxy-4H-chromen-4-one (S1-M10),
2-(2-(o-tolylamino)-4-aminothiazol-5-yl)-6-methoxy-4H-chromen-4-one (S1-M11),
2-(2-(2,6-dimethylphenylamino)-4-aminothiazol-5-yl)-6-methoxy-4H-chromen-4-one (S1-M12),
2-(2-(2,6-dichlorophenylamino)-4-aminothiazol-5-yl)-6-methoxy-4H-chromen-4-one (S1-M13),
2-(2-(4-methoxyphenylamino)-4-aminothiazol-5-yl)-7-methoxy-4H-chromen-4-one (S1-M14),
2-(2-(2-methoxyphenylamino)-4-aminothiazol-5-yl)-7-methoxy-4H-chromen-4-one (S1-M15).

3. The process for the preparation of compounds of formula (I) as claimed in claim 1, wherein said process comprising the steps of:
   a) reacting a mixture of substituted phenyl amine in water with carbon disulfide in presence of potassium carbonate by reaction with cyanuric chloride to afford substituted N-Phenyl isothiocynate;
   b) reacting N-Phenyl isothiocynate with guanidine in carbon tetrachloride by refluxing the mixture for the period in the range of 2-4 hrs to afford substituted 1-phenyl-3-formamidinothiocarbamide (intermediate 1);
   c) refluxing the reaction mixture of substituted 2-hydroxy acetophenone and chloroacetyl chloride in dimethyl formamide in presence of sodium chloro acetate at a temperature in the range of 185 to 195° C. to for the period in the range of 5 to 6 hr to afford 2-Chloromethyl-4-H-Chromen-4-one derivatives (intermediate 2);
   d) refluxing the solution containing compound of step (b) and compound of step (c) in methanol for a period in the range 4 to 6 hrs at a temperature in the range of 50 to 70° C. to afford compound of formula (I).

4. The process as claimed in claim 3, wherein said substituted phenyl amine compound is selected from phenyl amine, 4-methoxy phenyl amine, 4-nitro phenyl amine, 2-nitro phenyl amine, 4-Chloro phenyl amine, 3-(trifluoromethyl) benzenamine, 3,5-bis (trifluoromethyl) benzenamine, 4-(trifluoromethoxy) benzenamine, 2,4,6-trimethylbenzenamine and 4-bromo-2-fluorobenzenamine.

5. The process as claimed in claim 3, wherein said substituted N-Phenyl Isothiocynate compound is selected from phenyl isothiocynate, 4-methoxy phenyl isothiocynate, 4-nitro phenyl isothiocynate, 2-nitro phenyl isothiocynate, 4-Chloro phenyl isothiocynate, 2-isothiocyanato-1,3,5-trimethylbenzene and 4-bromo-2-fluoro-1-isothiocyanatobenzene.

6. The process as claimed in claim 3, wherein said substituted 1-phenyl-3-formamidinothiocarbamide compound is selected from 1-phenyl-3-formamidinothiocarbamide, 4-Methoxy Phenyl-3-formamidinothiocarbamide, 4-Nitro Phenyl-3-formamidinothiocarbamide, 2-Nitro Phenyl-3-formamidinothiocarbamide, 4-Chloro Phenyl-3-formamidinothiocarbamide, 2,4,6-trimethyl Phenyl-3-formamidinothiocarbamide and 2-Fluro,4-Bromo phenyl-3 formamidinothiocarbamide.

7. The process as claimed in claim 3, substituted 2-hydroxy acetophenone in step (c) is selected from 1-(2-hydroxyphenyl) ethanone, 1-(2-hydroxy-4-methylphenyl)ethanone, 1-(2,4-dihydroxyphenyl)ethanone, 1-(4-chloro-2-hydroxyphenyl)ethanone, 1-(4-fluoro-2-hydroxyphenyl) ethanone.

8. The process as claimed in claim 3, wherein said compound named intermediate 2 in step (c) is selected from 2-Chloromethyl-4-H-Chromen-4-one, 2-(Chloromethyl)-7-Hydroxy-4-H-Chromen-4-one and 2-(Chloromethyl)-6-Methoxy-4-H-Chromen-4-one.

9. A pharmaceutical composition comprising compound of formula (I) as claimed in claim 1 and at least one pharmaceutically acceptable carrier.

* * * * *